US008779763B2

(12) United States Patent
Bertacco et al.

(10) Patent No.: US 8,779,763 B2
(45) Date of Patent: Jul. 15, 2014

(54) SPINTRONIC MAGNETIC NANOPARTICLE SENSORS WITH AN ACTIVE AREA LOCATED ON A MAGNETIC DOMAIN WALL

(75) Inventors: Riccardo Bertacco, Morazzone (IT); Paolo Vavassori, Ferrara (IT)

(73) Assignee: Politecnico di Milano, Milan (IT)

( * ) Notice: Subject to any disclaimer, the term of this patent is extended or adjusted under 35 U.S.C. 154(b) by 464 days.

(21) Appl. No.: 12/989,576

(22) PCT Filed: Apr. 22, 2009

(86) PCT No.: PCT/EP2009/054808
§ 371 (c)(1),
(2), (4) Date: Oct. 27, 2010

(87) PCT Pub. No.: WO2009/130241
PCT Pub. Date: Oct. 29, 2009

(65) Prior Publication Data
US 2011/0037463 A1    Feb. 17, 2011

(30) Foreign Application Priority Data

Apr. 23, 2008  (IT) .............................. TO2008A0314

(51) Int. Cl.
*G01R 33/02*         (2006.01)
(52) U.S. Cl.
USPC .......................................... 324/244; 324/252
(58) Field of Classification Search
CPC .................... G01N 33/54346; G01R 33/1284; G01R 33/02; G01R 33/025; G01R 33/022; G01R 33/0385; B82Y 25/00
USPC ........................................................ 324/244
See application file for complete search history.

(56) References Cited

U.S. PATENT DOCUMENTS

| | | | |
|---|---|---|---|
| 5,945,825 A * | 8/1999 | Clemens ........................ 324/252 |
| 7,267,999 B2 * | 9/2007 | Drewes ............................. 438/3 |
| 8,399,229 B2 * | 3/2013 | Sooryakumar et al. ..... 435/173.9 |
| 2004/0262210 A1 * | 12/2004 | Westervelt et al. ........... 210/222 |
| 2006/0221677 A1 | 10/2006 | Klaeui et al. |
| 2007/0047156 A1 | 3/2007 | Cowburn et al. |

OTHER PUBLICATIONS

Allwood et al. "Mobile atom traps using magnetic nanowires", Jul. 6, 2006, Applied Physics Letters 89, 0104102 Rife et al. "Design and performance of GMR sensors for the detection of magnetic microbeads in biosensors", Nov. 1, 2003, Sensors and Actuators, vol. 107, Issue 3, pp. 209-218.*

(Continued)

*Primary Examiner* — Jermele M Hollington
*Assistant Examiner* — Hoang X Nguyen
(74) *Attorney, Agent, or Firm* — Jordan IP Law, LLC; Todd A. Vaughn (57) ABSTRACT

A sensor is described for detecting the presence of a magnetic nanoparticle (N). The sensor is arranged on a support (1), on which a plurality of non-magnetic contacts (Iin, GND, V1, V2) electrically conductively connected to the sensor is disposed. The contacts are adapted to be connected to means for measuring magnetoresistance. The sensor includes a planar ferromagnetic nanostructure (3), comprising a detection area (31) shaped as a strip bent to form a corner. The detection area is adapted to selectively assume, as a response to an applied magnetic field, a first spin configuration comprising a transverse "head-to-head" domain wall (TW), and a second spin configuration, wherein such domain wall (TW) is absent. The transition from the first configuration to the second configuration is affected by the proximity of a magnetic nanoparticle (N) to the detection area.

18 Claims, 7 Drawing Sheets

(56) References Cited

OTHER PUBLICATIONS

Yamaguchi et al. "Real-Space Observation of Current-Driven Domain Wall Motion in Submicron Magnetic Wires", Feb. 20, 2004, Applied Physics Letters 92, 077205.*

Himeno et al. "Dynamics of a magnetic domain wall in magnetic wires with an artificial neck", May 15, 2003, Journal of Appies Physics 93, No. 10.*

McGrouther et al. "Controlled domain wall injection into ferromagnetic nanowires from an optimized pad geometry", Jul. 12, 2007, Applied Physics Letters 91, 022506.*

P. Vavassori et al., "On-chip manipulation of magnetic nanoparticles through domain walls conduits," arXiv.org, Mar. 20, 2009.

P. Vavassori et al., "Domain wall displacement in Py square ring for single nanometric magnetic bead detection," Applied Physics Letters, vol. 93, No. 20, Nov. 17, 2008.

L.E. Helseth et al., "Domain wall tip for manipulation of magnetic particles," Physical Review Letters, vol. 91, No. 20, Nov. 14, 2003.

L.E. Helseth et al., "Paramagnetic beads surfing on domain walls," Physical review. E, statistica, nonlinear, and soft matter physics Apr. 2003, vol. 67, No. 4 Pt 1.

* cited by examiner

SPINTRONIC MAGNETIC NANOPARTICLE SENSORS WITH AN ACTIVE AREA LOCATED ON A MAGNETIC DOMAIN WALL

CROSS REFERENCE TO PRIOR APPLICATIONS

The present application is a National Stage Application of PCT International Application No. PCT/EP2009/054808 (filed on Apr. 22, 2009), under 35 U.S.C. 371, which claims priority to Italian Patent Application No. TO2008A000314 (filed on Apr. 23, 2008), which are each hereby incorporated by reference in their respective entireties.

BACKGROUND

1. Technical Field

The present invention generally refers to magnetic nanoparticle sensors and to molecular recognition procedures, suitable for applications in several different fields.

As such, the biomolecular recognition is the interaction between biomolecules, which have a mutual affinity or present some sort of complementarity. Examples of such interactions are the DNA-DNA hybridization, the antibody-antigen recognition and the ligand-receptor bond [H. A. Ferreira et al., IEEE Transactions on Magnetics 41, 4140 (2005)].

2. Description of the Related Art

The biomolecular recognition is, actually, omnipresent in life, as it constitutes the way the cell mechanisms work. Evident examples are the genetic code replication, the enzyme generation, protein glycids and nucleic acids fabrication and modification, the intracellular and extracellular transport, the cellular metabolism, to mention some of the most common biological processes. On the other hand, more familiar uses of the biomolecular recognition comprise pregnancy tests, blood group verification, genetic screening and site-directed cancer treatments, currently under development. It is clear that the biomolecular recognition detection is more and more important in fields such as healthcare, pharmaceutical industry, environmental analysis, and in general in biotechnological applications.

In general, the detection results in the usage of a known biomolecule which probes a test sample, looking for a specific target analyte. A common approach for detecting biological molecules is to attach a marker to the target molecule, which produces an externally observable signal. Traditionally, this is implemented by using a molecular recognition between the target molecule and a specific receptor (for example an antibody) labelled by the marker. The marker can be a radioisotope, an enzyme or a fluorescent molecule, as in case of the LIF (Light Induced Fluorescence) techniques. Recently, as markers for the bio-detection, magnetic microparticles and nanoparticles have also been used, due to their advantages in respect to the other markers. The magnetic properties of the nanoparticles are stable over the time, since the magnetism is neither affected by the chemistry of the reagents, nor subject to photobleaching (a problem related to the use of fluorescent markers). Moreover, in biological applications, generally, there is no significant magnetic background signal, and the magnetic fields are not screened by reagents or aqueous biomaterials. Moreover, magnetism can be used to remotely handle the magnetic particles. It is to be highlighted that the sizes of the magnetic particles shall be as reduced as possible for introducing as little perturbation as possible in relation to the affinity between the probe molecules and the target molecules. In any case, it is necessary to find a compromise between the latter aspect and the need of a magnetic moment, dimensioned such that it can be detected by a specific sensor with a proper signal-to-noise ratio. Until now, several research groups have used particles with a diameter from a few microns to 16 nm.

In the last years, a lot of very sensible magnetic fields detecting devices have been developed, such as giant magnetoresistance (GMR) [M. N. Baibich et al., Phys. Rev. Lett. 61 (21), 2472-2475 (1998)] and spin valve magnetic sensors [B. Dieny et al., J. Appl. Phys. 69(8), 4774 (1991); P. P. Freitas et al., Sens Actuat A Phys, 81 (1-3), 2 (2000)] which allow extremely weak magnetic fields to be measured, such as those generated by a single magnetic microparticle. Beside the GMR sensors, detection of single magnetic particles has been demonstrated with miniaturized silicon Hall sensors [P. A. Besse et al., Appl. Phys. Lett. 80 (22), 4199 (2002)] and planar Hall effect sensors, based on thin Permalloy films (FeNi alloy) [L. Ejsing et al., Appl. Phys. Lett. 84 (23), 4729 (2004)]. More recently, tunnel magnetoresistance (TMR) sensors have been applied to the molecular recognition, based on magnetic tunnel junctions (MTJ) [W. Shen et al., Appl. Phys. Lett. 2008, 103, 07A306], due to their superior sensibility and stability in relation to temperature. The use of anisotropic magnetoresistance in ring sensors, as sensitive particle detectors, has been suggested by Miller et al. [M. M. Miller et al., Appl. Phys. Lett. 81, 2211 (2002)] and, more recently, such an approach has been extended by L. Llandro et al. [L. Llandro et al., Appl. Phys. Lett. 91, 203904 (2007)] to multi-layer ring sensors (pseudo-spin valve) based on the giant magnetoresistance (GMR) effect. In the first case, the ring sensor was made of NiFe and it was designed to detect the radial component of the field created by a single microsphere (diameter 4.3 microns), magnetized by an alternating magnetic field. In the second case, the detection of a superparamagnetic microsphere with a diameter of 4 microns was reported, by using a pseudo-spin valve ring sensor. In absence of the particle, the magnetization of the sensor free layer is modified by a periodical external magnetic field, so that, every time an anti-parallel alignment configuration of the magnetic layers is established, a GMR peak is generated. Once a magnetic particle is placed on the sensor, the particle screens the external magnetic field, and causes a change of the external fields needed for the reversal of the free layer. In order to compare several sensors for the biomolecular recognition, the following parameters have to be taken into account:

1) Biological sensitivity—it corresponds to the ability to detect low concentrations of the target analyte in biological samples, and it is normally given in terms of limit of detection (LOD); a low LOD corresponds to a high biological sensitivity;

2) Dynamic range—such a parameter indicates the analyte concentration range, which can be detected by the sensor, operating on a linear regime in a given biological assay.

In some cases, the biological sensitivity is not a problem, as amplification processes, which enable an increase in the analyte concentration, such as the polymerase chain reaction (PCR), for the DNA in genomics, can be applied. In other applications (such as proteomics), however, there are no suitable methods for amplification, therefore a high biological sensitivity is required.

The dynamic range is a feature, which is often in competition with the biological sensitivity. Sensors, designed for detecting individual particles, are not able to count large numbers of molecules, so their application in analyte concentration measurements becomes troublesome.

Moreover, the paper of P. Vavassori et al., Appl. Phys. Lett 91, 093114 (2007), regarding square rings of Permalloy applied in the magnetic storage field, is useful to fully understand the teachings of the present invention.

SUMMARY OF THE INVENTION

In view of the above mentioned problems, it is an object of the invention a sensor for detecting the presence of a magnetic nanoparticle as defined by the appended claim 1. Particular embodiments of the sensor are depicted by the dependent claims.

It is a further object of the invention a sensor array for detecting target molecules as defined by the enclosed claim 6. Particular embodiments of the sensor array are defined by the dependent claims 7-10.

It is a further object of the invention a method for detecting target molecules as defined by the appended claim 11.

According to particular examples, the sensor, the sensor array and the detection method according to the invention are based on the electric resistance variations, due to the variations in the magnetization configuration in a nanostructure (anisotropic magnetoresistance effect, AMR), in particular in an area confined to the vertex of a corner of such a nanostructure (detection area). The magnetization configuration can be handled in a controlled manner by applying an external field and unambiguously probed through magnetoresistive measurements. The clarity and high predictability of the transition between different magnetization configurations allow to use the nanostructure for detecting nanoparticles. The proximity of a magnetic nanoparticle, affects the values of the external field required to modify the magnetization configuration, thereby providing a practical way to detect the presence thereof.

On one hand, the detection of a single molecule marked with a small nanoparticle can be obtained, since the effect of an individual magnetic nanoparticle on the micromagnetic configuration of the nanostructure is strong enough. This is due to the fact that the domain wall and the magnetic particles have comparable dimensions.

Further, multiple sensors can be arranged in an array according to configurations of nanostructures, which allow an effective detection and counting of multiple magnetic nanoparticles, allowing a quantitative definition of the molecular concentration in biological samples, with very low obtainable detection limits.

BRIEF DESCRIPTION OF THE DRAWINGS

Further characteristics and advantages will result from the following description, with particular reference to the attached drawings, given only by way of example, and not limiting, wherein:

FIG. 7b shows a vector diagram of the force acting on a superparamagnetic nanoparticle with a diameter of 50 nm on a plane at 200 nm from the top surface of the initialized device, as in FIG. 2a;

DETAILED DESCRIPTION

The devices and the methods described in the scope of the present invention relate to nanostructures. Typically, the nanostructures are structures having at least two dimensions smaller than 1 µm (for example nanometric dimensions). Even though the exact boundaries of the nanostructure class cannot, actually, be defined by a particular numerical dimension value, such a class is however clearly recognizable by those skilled in the art.

The present invention relates to a sensor for detecting single magnetic nanoparticles and a sensor array for detecting a plurality of magnetic nanoparticles. As it will be more clear from the hereinafter description, the described sensor can be employed to perform single molecule detection and/or employed in systems for synthesis at a single molecule level and/or analysis at a single molecule level. The sensor array is employed for detecting the concentration of target molecules, to which magnetic nanoparticles are linked, as markers.

The biosensor array conventionally comprises a support 1, on which a plurality of detection sites is disposed (indicated by DS in FIGS. 10a and 10b), to which respective binding molecules are associated, adapted to selectively bind to the target molecules.

To the end of the present invention, the term "binding molecule" refers, for example, to antibodies, strands of polynucleic acids (DNA or RNA) or molecular receptors capable of selectively binding to, that is to "recognize", potential target molecules, such as, for example, polynucleic acids, enzymes, proteins, peptides, antibodies, metal ions, exc., of which it is desirable to determine the presence, absence or concentration in an assay.

Figure 1:
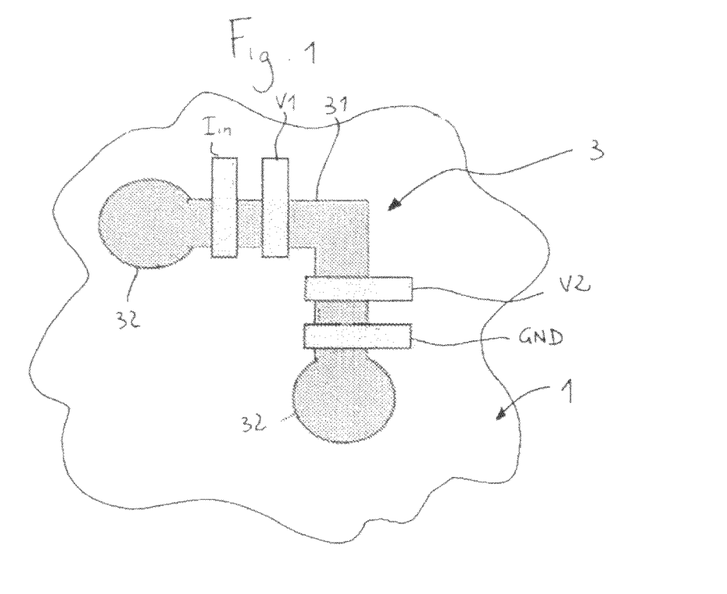
FIG. 1 is a simplified plan view, which illustrates a single sensor according to the invention.

In FIG. 1, a single sensor arranged on a support 1 is represented, which includes a ferromagnetic planar structure 3. Such a nanostructure 3 is typically covered by a plurality of layers (not shown) provided for a biosensor, comprising an insulating protective layer, a polymeric layer for attaching the above mentioned binding molecules, and the layer of binding molecules. The nanostructure 3 comprises at least one detection area 31 shaped as a strip bent to form a corner. More particularly, the detection area 31 corresponds to a vertex of such corner.

The nanostructure 3 comprises also a couple of terminal discs 32, obtained at the opposite ends of the detection area 31. The nanostructure 3 is for example made of Pennalloy. In the numerical examples, which will be provided below, reference will be made to a nanostructure made of such a material, having a thickness of 40 nm and a width of the strip in the detection area of 50 nm, and total external dimensions of 0.3 μm×0.3 μm. Such dimensions, however, can be further reduced without detriment for the device functionality.

On the opposite ends of the detection area 31, a plurality of non-magnetic contacts Iin, GND, V1 and V2, is arranged which can be obtained, for example, through electron beam lithography on the surface of the nanostructure 3. The contacts Iin, GND, V1 and V2 are adapted to be linked to measuring means (not illustrated) suitable for measuring the magnetoresistive response of the nanostructure 3 at the ends of the detection area 31. In particular, in the specific illustrated example, two supply contacts Iin and GND are present, adapted to be linked to a current supply circuit, to inject an electric current through the detection area 31, and two reading contacts V1 and V2, adapted to be linked to a measuring circuit, for measuring the potential difference between the ends of the detection area 31. The above mentioned contacts are, for example, made of Au.

Figure 2A:
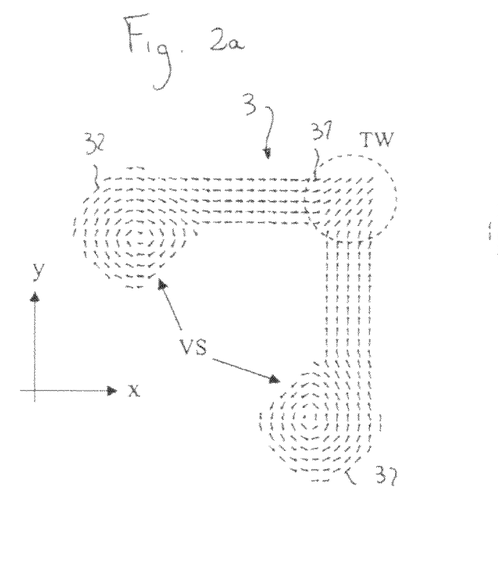
FIG. 2a illustrates the sensor of FIG. 1 in a first spin configuration with a transversal head-to-head domain wall on a corner of the sensor and vortex configuration on terminal discs.
Figure 2B:
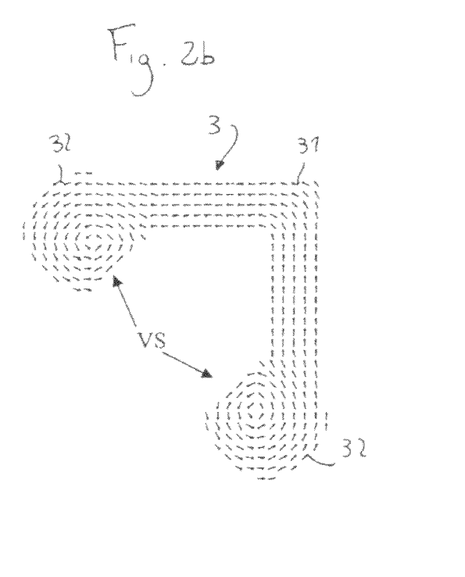
FIG. 2b illustrates said sensor in a second spin configuration, wherein the domain wall of FIG. 2a is annihilated, by applying a magnetic field parallel to one of the corner sides, with a higher intensity than a predetermined threshold, and subsequently removing such a field.

Referring to FIGS. 2a and 2b, the two spin configurations, which can be induced in the nanostructure 3 by applying a magnetic field along the bisector of the angle formed by the two sides of the bent structure (FIG. 2a) or parallel to one of the sides (FIG. 2b) are shown. Below, for sake of simplicity, reference will be made to the Cartesian coordinate system, x, y, respectively parallel to the sides of such an angle.

In FIG. 2a, a first configuration is illustrated, and it comprises a magnetic transversal head-to-head domain wall TW positioned at the corner of detection area 31 and vortex structures VS, formed inside the terminal discs 32. The application of a second magnetic field along the direction x or y, displaces the domain wall TW towards one of the terminal discs 32, where it is annihilated in the vortex spin structure, resulting in the second configuration illustrated in FIG. 2b.

Figure 3:
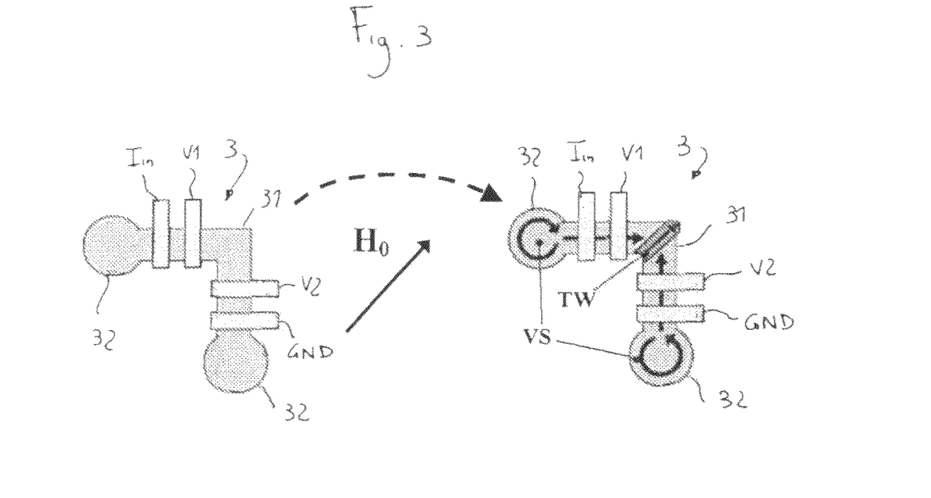
FIG. 3 illustrates an initialization operation of the device in FIG. 1.

FIG. 3 shows an example of the method for initializing the device, according to which the transversal "head-to-head" domain wall TW is positioned in the angle of the detection angle 31, by applying a magnetic field $H_0$ (with and intensity, for example, of 1000 Oe) along the angle bisector and subsequently removing such a field. At the same time, on the terminal discs 32, the two vortex spin structures VS are implemented. Once it has been created, the domain wall TW is stable, and it can be displaced until it is annihilated in one of the vortex spin structures, by applying a magnetic field along the direction x or y.

Figure 4:
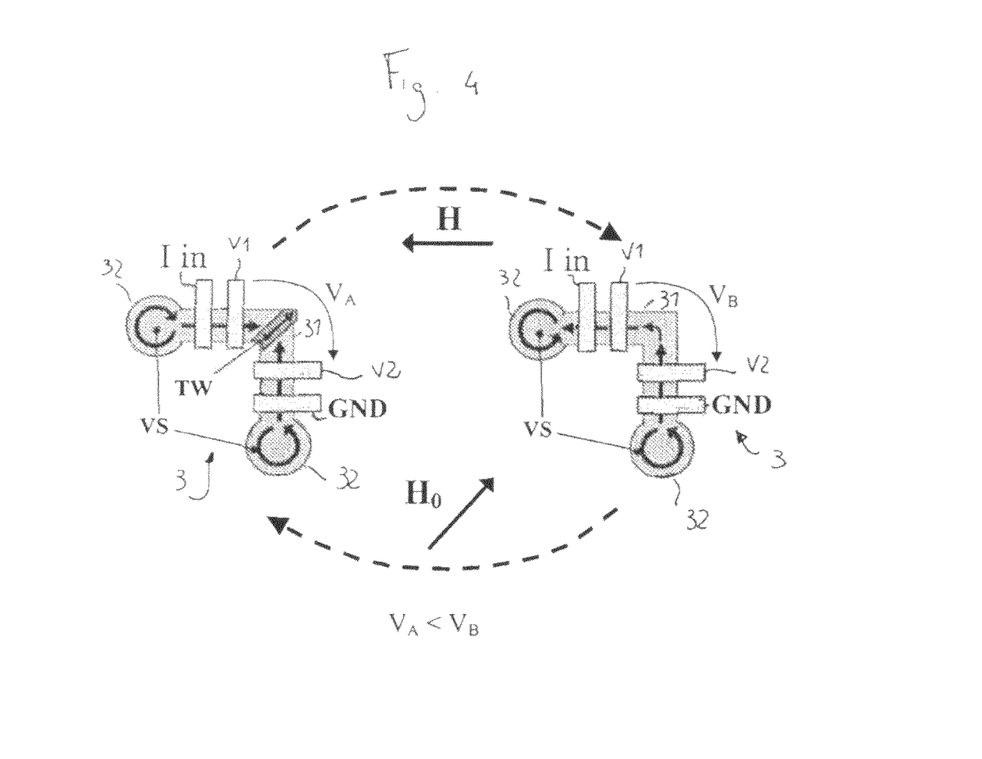
FIG. 4 illustrates the switching of the device in FIG. 1 between the spin configurations in FIGS. 2a and 2b.

FIG. 4 shows the removal of a domain wall TW from the corner, by applying a horizontal magnetic field (direction x) H. The domain wall TW can be relocated on the angle, by applying a horizontal magnetic field on the opposite direction, or by applying again a field $H_0$ along the bisector of the angle, as illustrated in FIG. 4.

For detecting the presence of a domain wall TW in the corner of the nanostructure, magnetoresistive measurements are employed, i.e. the measurement of the potential differences $V_A$ and $V_B$ between the reading contacts V2 and V1, respectively, in the two spin configurations illustrated in FIG. 4 (corresponding to those in FIGS. 2a and 2b, respectively). The magnetoresistance in the nanostructures according to the invention is controlled by the so-called anisotropic magneticresistance effect (AMR), and a maximum resistance is observed (and therefore a maximum potential difference between the reading contacts) when the magnetization is parallel or anti-parallel to the injected flow of current. This corresponds to a condition where there is no domain wall between the two reading contacts V2 and V1, and the magnetization continuously rotate following the corner shape in the detection area 31, resulting in the potential differential $V_B$ in FIG. 4.

If, between the reading contacts V2 and V1, there is a domain wall TW, magnetization is partly directed perpendicularly to the current flow and therefore the resistance is lower, resulting in the potential differential $V_A < V_B$, as shown in FIG. 4.

The high predictability in switching between the two spin configurations and the sharpness of the transition between such configurations allow the nanostructure to be used for detecting the magnetic nanoparticles, as follows.

Figure 5:
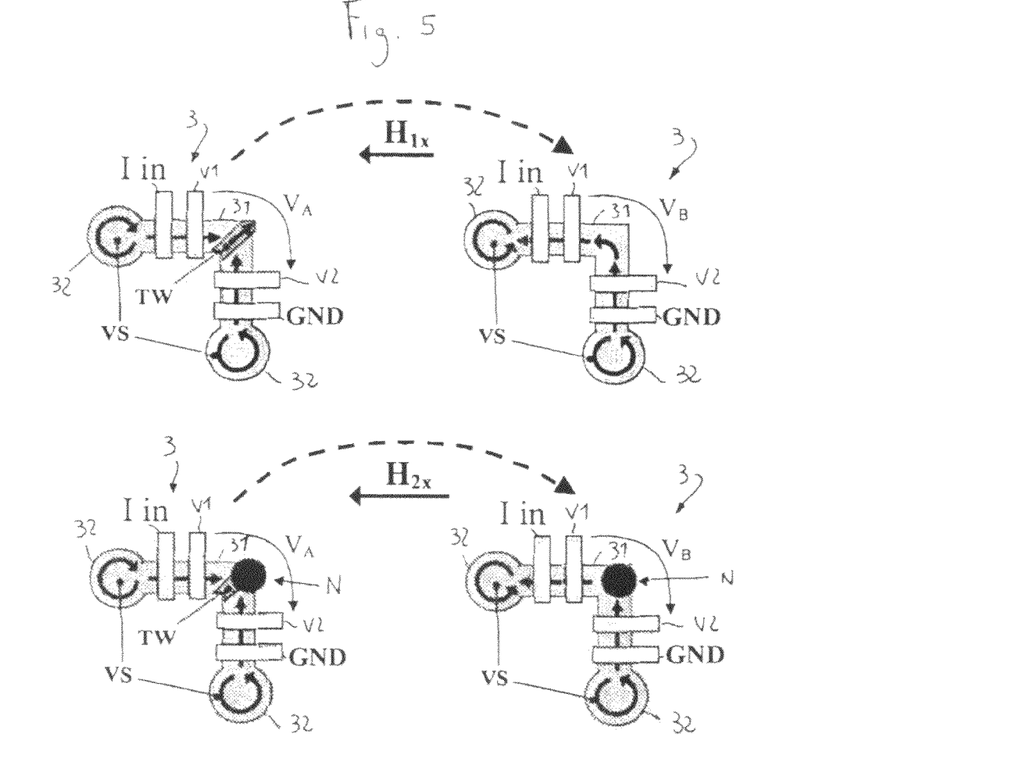
FIG. 5 illustrates an operation principle of the device in FIG. 1, for detecting a magnetic nanoparticle.

The required field for displacing the domain wall TW from the vertex of the detection area 31, resulting into its annihilation in one of the two vortex spin structures VS has a well-defined threshold value, particularly, $H_{1x}$ in FIG. 5 for a field H applied horizontally. If a magnetized nanoparticle N is placed in proximity to the corner where the domain wall TW is located, the dipolar interaction between the field generated by the domain wall TW and the magnetic moment of the particle N, prevents the domain wall TW from moving at $H_{1x}$, so that in order to switch the magnetization in the horizontal segment of the nanostructure 3, a higher field intensity $H_{2x}$ is required, as shown in FIG. 5. The magnetic field intensity required for moving and annihilating the domain wall TW, observed by measuring the potential difference between the two reading contacts V2 and V1, can be used to detect the proximity of a magnetic nanoparticle N.

Figure 6:
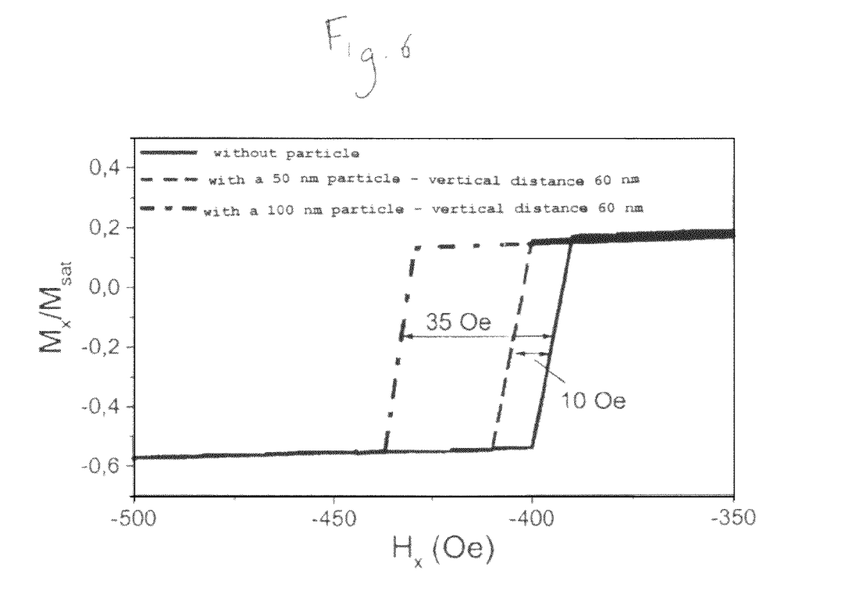
FIG. 6 is a graph, which shows the magnetic field, required for annihilating the spin configuration of FIG. 2a, in absence of magnetic nanoparticles (solid line), and with a superparamagnetic nanoparticle (magnetic particle which acquires a magnetic moment only in presence of an external field) arranged on the domain wall at a vertical distance of 60 nm from the nanostructure surface, having a diameter of 50 nm (broken line) and 100 nm (broken and dotted line), respectively.

In FIG. 6, the result of a simulation of the effect of a commercial magnetic nanosphere MACS™ NPs (diameter 50 nm, saturation magnetization Ms=300 emu/cm$^3$) is shown, placed above the domain wall TW, with the bottom thereof at a vertical distance of 60 nm from the surface of the nanostructure of Permalloy. Such a distance corresponds to a predictable thickness for a biosensor, taking into account the layers which cover the nanostructure 30, which is the insulating protective layer, the intermediate polymeric layer and the binding molecule layer (for example, in case of probe molecules formed by DNA strands, the length of such filaments is taken into account). Because of the proximity of the nanoparticle N, the displacement of the TW by a horizontally applied field is retarded by 10 Oe (broken line in FIG. 6) in respect to the case of the angle without nanoparticles (solid line in FIG. 6). FIG. 6 also shows the effect of the particle diameter on the field, which causes the structure TW to move: using a nanoparticle with a diameter of 100 nm positioned at a vertical distance of 60 nm from the surface of the nanostructure, such a field increases by 35 Oe (broken and dotted line in FIG. 6).

An evaluation for the signal-to-noise ratio, corresponding to the detection of the displacement of the domain wall TW from the corner, can be obtained by previous tests carried out in case of a domain wall TW, displaced between two adjacent angles of a square ring nanostructure of Permalloy [P. Vavassori et al., Appl. Phys. Lett. 91, 093114 (2007)]. The measurements were carried out by injecting an alternating current of 15 μA (473 Hz frequency) in the annular structure and by measuring the potential difference between the two Au contacts at the ends of a corner with a lock-in amplifier (time constant of 10 ms). A domain wall TW was positioned in the selected corner with an external magnetic field, applied along one of the sides of the ring, i.e. following the same procedure described in relation to the corner-shaped nanostructure 3 described herein. The inventors have detected a variation (increase) in the potential difference by 1.45 μV, after removal of the TW from the angle with a noise (with and without the domain wall TW) of 60 nV, corresponding to a signal-to-noise ratio of 24 (which increases to about 60, increasing the time constant of the lock-in amplifier, i.e. the integration range, up to 100 ms). This value can be used as a good evaluation of the typical signal-to-noise ratio, which characterizes the detection process of the nanoparticles by the device described herein.

For practical applications, the device can be operated as follows: first it is initialized, by positioning a domain wall TW in the angle, as shown in FIG. 3 (the possible presence of the nanoparticle does not affect such a step); a horizontal field $H_k$ is then applied, so that $H_{1x} < H_k < H_{2x}$; if the potential difference between the two reading contacts V2 and V1 does not change, a magnetized nanoparticle N is sitting on top of the corner; on the contrary, if the potential difference changes (i.e. increases) no nanoparticles are localized on the sensor active area.

Importantly, it is to be noted that the active area of the device is only the angle portion occupied by the domain wall TW, which is in the same length order as the detection area 31 of the strip, i.e. 50 nm×50 nm in the concerned example, and it coincides with the portion of the nanostructure 3 included between the reading contacts V2 and V1. Therefore, for detecting a single nanoparticle, the detection area 31 can be adapted to the dimensions of the nanoparticle to be detected, by designing, as a consequence, the width of the bent strip without having to reduce the whole nanostructure 3.

Figure 7A:
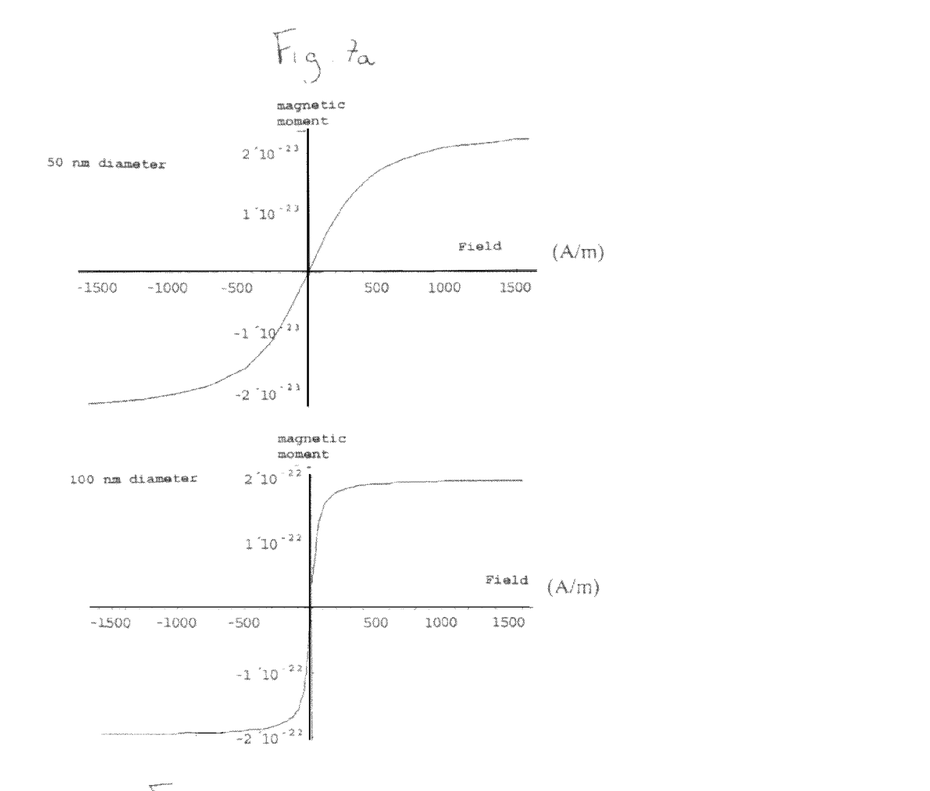
FIG. 7a illustrates graphs which represent the magnetic moment of spherical superparamagnetic particles having a diameter of 50 nm and 100 nm (and saturation magnetization of $3 \cdot 10^5$ A/m), as a function of the applied field.
Figure 7B:
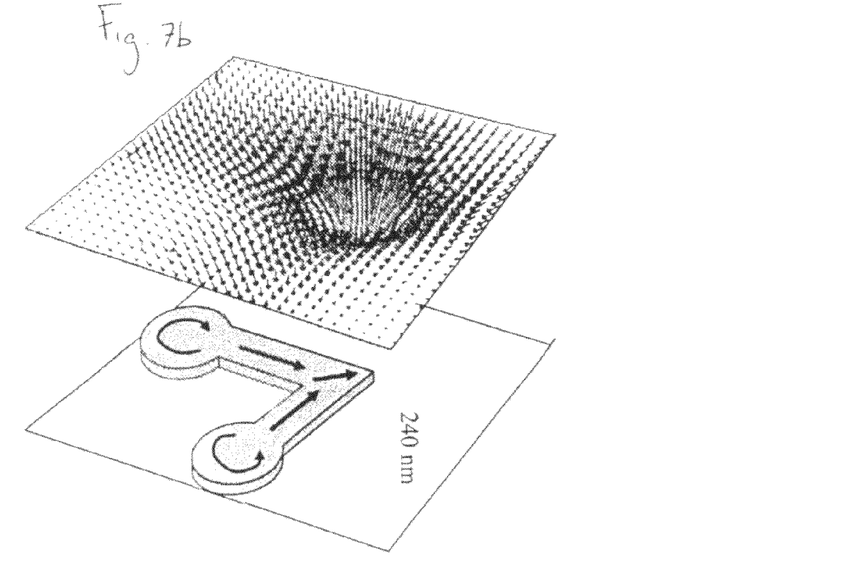

Another condition to be fulfilled for the correct functioning of the device requires that the nanoparticle is placed proximate to the vertex. The effective concept of the device with two terminal discs 32 provides that, when the sensor is initialized at the magnetic state, represented in FIG. 2a, there is a magnetic field created by the nanostructure 3, uniquely around the domain wall TW, whereas, somewhere else, the field is negligible (the vortex spin structure VS does not result into a considerable field). The high field gradient, which characterizes such a dispersion field guarantees that a demagnetized particle, in the vicinity of the structure, can be trapped and trailed towards the detection area 31 (autofocusing). FIG. 7b shows the vector diagram of the force acting on a plane spaced 200 nm from the surface of the sensor on a superparamagnetic nanoparticle with a diameter of 50 nm, characterized by a magnetic moment as a function of the external field, m(H), as shown in the top graph in FIG. 7a, which is the estimated value for the commercial nanoparticle MACS™, herein taken into account. The bottom graph in FIG. 7a shows also m(H) for a nanoparticle MACS™ with a diameter of 100 nm. The force was computed by computing the magnetic field, created in the surrounding space from the nanostructure in the magnetic configuration in FIG. 2a and by applying the following vector expression:

$$F = \mu_0 (m \cdot \nabla) H,$$

the magnetic moment of the nanoparticle being m=L(H, T, V, $M_s$)$VM_s$h, wherein V and $M_s$ are the volume and the saturation magnetization, respectively, of the nanoparticle, h is a versor parallel to the applied field H, and L(H, T, V, $M_s$) is the Langevin function, which describes the superparamagnetic behaviour of the nanoparticle. The vector diagram in FIG. 7b clearly shows that the nanoparticle would be trailed towards the angle of the nanostructure, wherein a domain wall TW is positioned.

Figure 8:
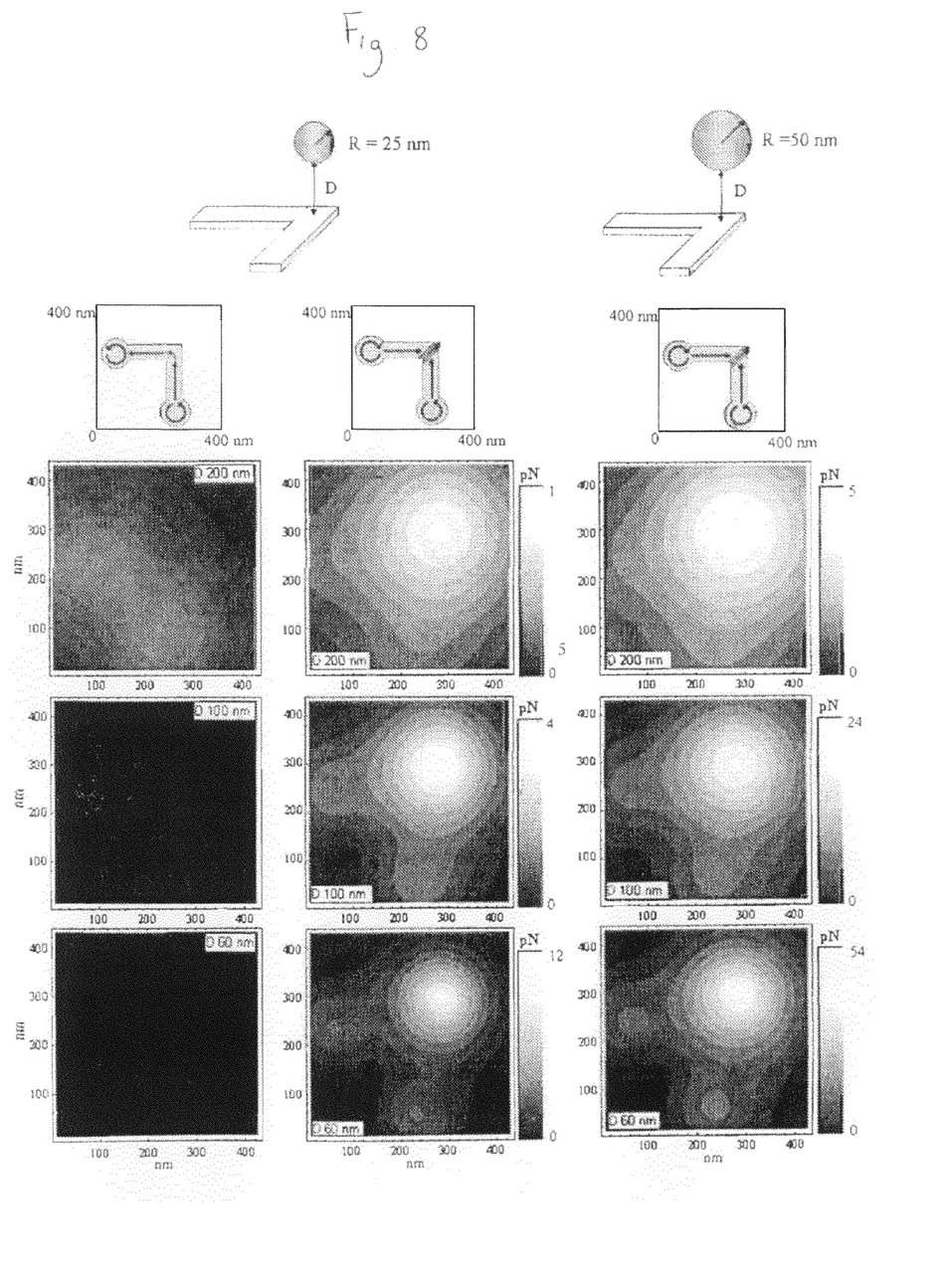
FIG. 8 is a set of intensity contour plots of the attractive force acting on a superparamagnetic nanoparticle (whose magnetic moment in function of the field is represented in FIG. 7a) with a diameter of 50 nm and 100 nm, respectively, on planes at 200, 100 and 60 nm from the surface of the nanostructure, with the spin configuration of FIG. 2a (central and right column), and after the annihilation of such a configuration (left column)

FIG. 8 shows the level curve diagrams of the module of the force acting on a superparamagnetic nanosphere having a diameter of 50 nm or 100 nm on planes at 200, 100 and 60 nm from the surface of the nanostructure 3, with the domain wall TW in the angle (central and right column in FIG. 8) and after annihilation of the domain wall TW (left column in FIG. 8). The level curve diagrams in the central column in FIG. 8 show that the module of the force acting on the nanoparticle with a 50 nm diameter at a distance of 200 nm from the nanostructure 3 is in the range from 0.5 to 1 pN on an area with a diameter of about 300 nm, guaranteeing effective trapping and focusing actions on a nanoparticle (see the explanation below). The module of the force increases by a factor of about 10 if the distance between the nanoparticle and the surface of the nanostructure is reduced to 60 nm. The intensity contour plots in the left column in FIG. 8 show that when the domain wall TW is removed from the corner and annihilated in one of the vortex spin structures VS, the force acting on the nanoparticle at the angle is negligible.

Therefore, oppositely in respect to the other devices, no external action is required (such as the positioning of the nanoparticle in the correct position, by using an external field inducing also a momentum in the nanoparticle), in order to position and magnetize the particle for an optimal detection. The force acting on a nanoparticle can be increased or decreased, by increasing or decreasing the nanostructure thickness, respectively. Such an aspect is critical in setting the magnetic focusing and to prevent the particles from grouping, which can result in case of fields with a too high gradient.

Such a problem of magnetic focusing in respect to the conventional magnetic focusing obtained with current lines consists in that it is permanent and that the magnetic force could hinder the chemical bond between binding molecules and the target molecules, resulting in compromising the biological assay specificity. An approximate evaluation of the energy of the magnetic bond of a nanoparticle positioned above the domain wall TW gives $10^{-18}$ J, to be compared with the comparable value of the bond energy between the two helix portions for a typical hybridization reaction DNA_DNA, taking into account an oligo with 23 basis, which is $8 \cdot 10^{-19}$ J. These values clearly indicate that a permanent focusing would not be acceptable. However, in the concept according to the invention, the domain wall TW may be annihilated in the terminal discs, by simply applying an external field, thereby obtaining a condition, wherein the magnetic forces are negligible, as discussed above, with reference to the diagrams in the left column in FIG. 8. In other words, the concept according to the invention allows to activate and deactivate the magnetic focusing, through external fields, without additional current lines, which would increase the device complexity.

The biosensor array could then operate as follows:
 (i) a domain wall TW is placed on the detection area 31 of each nanostructure 3, and the biological sample is spread on the area occupied by the sensors, such to allow the magnetic nanoparticle auto-focusing on the detection area 31 in each nanostructure 3;
 (ii) the domain walls TW are annihilated in the respective terminal discs 32, thereby removing the magnetic forces;

(iii) the target molecules and the non-selectively chemically bound nanoparticles are removed from the detection sites DS, through a conventional washout process;

(iv) the domain walls TW are placed again in the detection areas 31, through an external magnetic field, and the presence of a specifically bound target molecule is detected, due to the measure of the critical transition field, from said first spin configuration TW into said second spin configuration, wherein the domain wall TW is annihilated in one of the vortex structures VS, through the measure of the critical transition field, determined, in turn, according to a measure of the potential difference at the ends of contacts V1 and V2.

Figure 9:
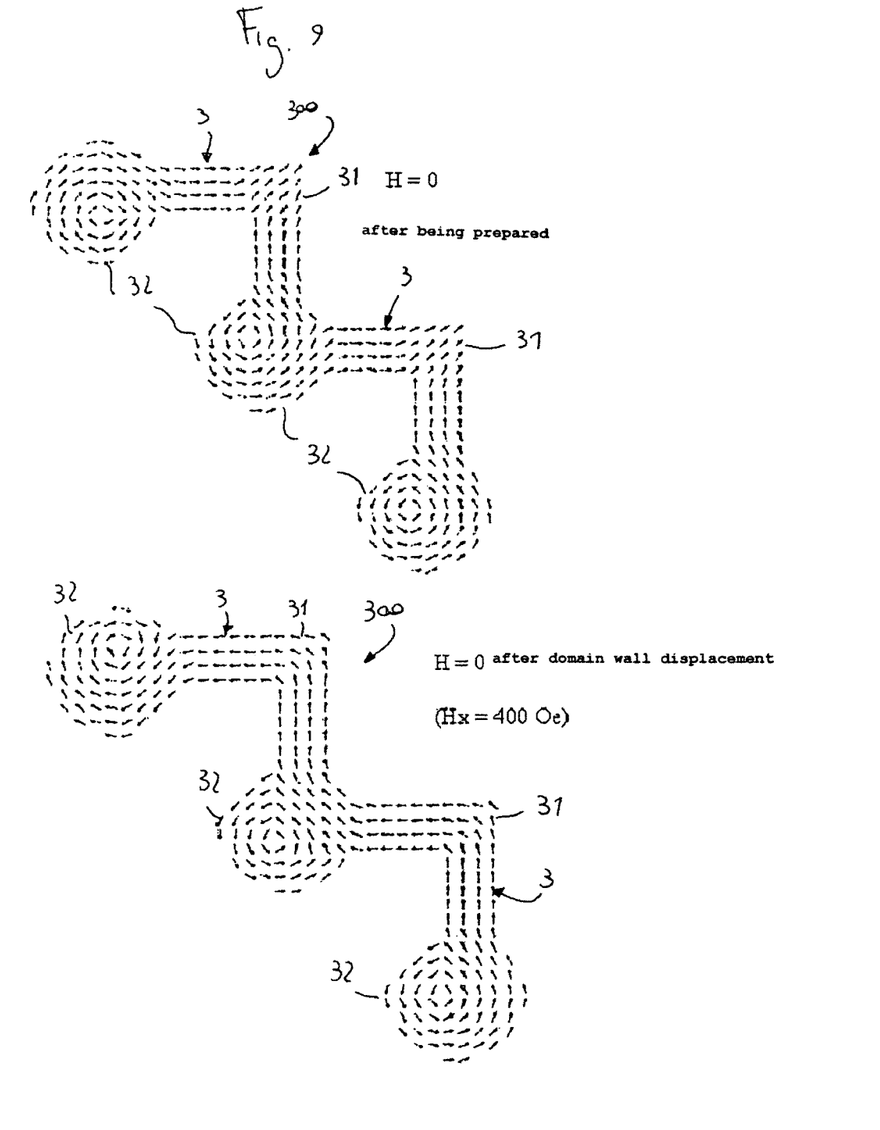
FIG. 9 represents micromagnetic simulations of two nanostructures according to FIG. 1, linked to each other.

FIG. 9 shows micromagnetic simulations, which illustrate how the corner structure can be repeated in chains, without altering the operation of each unit. Practically, a chain 300 is made by causing each individual nanostructure 3 to share a proper terminal discs 32 with another nanostructure 3 adjacent thereto. Such a configuration is particularly suitable to make an array, arranging a plurality of chains 300 of side-by-side nanostructures. Due to the excellent signal-to-noise ratio, which characterizes the nanoparticle detection process (same as or higher than 24, as described above), and for reducing the number of required contacts for counting a plurality of nanoparticles, the potential difference can be read in a plurality of detection areas 31, linked by reading contacts, such to form a set of resistances in parallel (FIG. 10*a*) or in series (FIG. 10*b*). In particular, in FIG. 10*a*, part of an array is illustrated, wherein among the side-by-side chains 300, pairs of reading contact strips 310, 320 extend (corresponding to the reading contacts V1 and V2, previously described), wherein each detection area 31 of each nanostructure chain 300 is connected in parallel with a detection area 31 of the other nanostructure chains 300 corresponding thereto for the position, through a respective pair of reading contact strips 310, 320. The chains 300 are supplied in parallel through supply contacts Iin and GND. On the other side, in FIG. 10*b*, part of an array is illustrated, wherein a pair of reading contact strips 410, 420 (corresponding to the reading contacts V1 and V2, previously described), is connected to the opposite ends of each chain 300 on all the chains 300. The chains 300 are independently supplied by respective injection contacts (with the index i=1, 2, 3, 4 . . . ), with a common current output contact GND. In any case, for reading on multiple detection areas 31, each pair of reading contact strips 310, 320 (in the configuration in FIG. 10*a*) or each current injection contact $Ii_{in}$ must be sequentially enabled by a multiplexer. In order to ensure an independent reading of the single chains, the impedance of the reading strips 410 and 420 shall be significantly higher than that of the chains. The above computed signal-to-noise ratio is such that it can be predicted to have up to 5 detection areas 31, connected in parallel or in series between two reading contacts.

In order to obtain a high biological sensibility, the sensor active area (matching with the detection area 31) and the functionalized area (i.e. the area occupied by the binding molecules arranged above the sensors) should match. The selective functionalization of the individual detection area 31, however, is extremely difficult and not suitable for a large-scale production of the devices; it is, indeed, more reasonable, to assume a functionalized area in the order of 200 $\mu m^2$, wherein several units of the array can be grouped, such as those represented in FIGS. 10 and 10*b*. However, this does not result in a significant loss of biological sensibility, as the auto-focusing tends to concentrate the magnetic nanoparticles on the detection areas 31. The typical forces obtained by the current line used for the magnetic focusing of the nanoparticles on the active area of the devices, are in the order of fractions of pN, as reported in the article by Ferreira et al. [H. A. Ferreira et al., Appl. Phys. Lett. 87, 013901 (2005)]. According to this, it can be assumed that the capture area in case of nanoparticles with a diameter of 50 nm is a circle, wherein the nanoparticle force is higher than 0.5 pN at a height of 200 nm (the maximum distance taken into account in the simulations in FIG. 8). The so-computed capture areas are reported as grey circular areas in FIGS. 10*a* and 10*b*. It is observed, then, that more than 75% of the functionalized area corresponds to the actual active area of sensors. For larger nanoparticles (for example with a diameter of 100 nm) or for nanoparticles with a higher saturation magnetization value, the situation could be even more favourable and the capture area could entirely cover the functionalized area. The force acting on the nanoparticle is likely to be sufficiently high to guarantee that the latter would be drawn towards a detection area 31, where the presence thereof can be detected, for any initial position on the functionalized area, but this result needs to be experimentally confirmed. Moreover, if required, the intensity of the magnetic force and the capture area extension can be adjusted in many different ways: (i) changing the thickness and/or the width of the nanostructure 3 strip, or (ii) modifying the angle between the two segments, which define the corner. Reducing the thickness results, for example, in an increase of the variation in the transition field, caused by the vicinity of the magnetic nanoparticle (magnetic signal), even though such an advantage is accompanied by a decrease in the focusing magnetic forces.

Figure 10A:
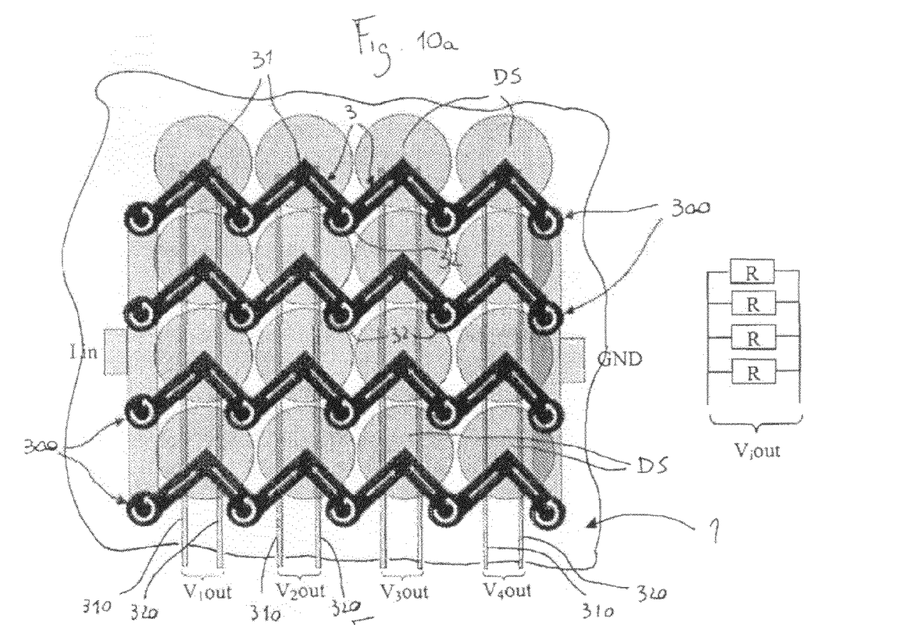
FIGS. 10a and 10b schematically show a portion of a sensor array of FIG. 1, according to a configuration in parallel and according to a configuration in series, respectively.
Figure 10B:
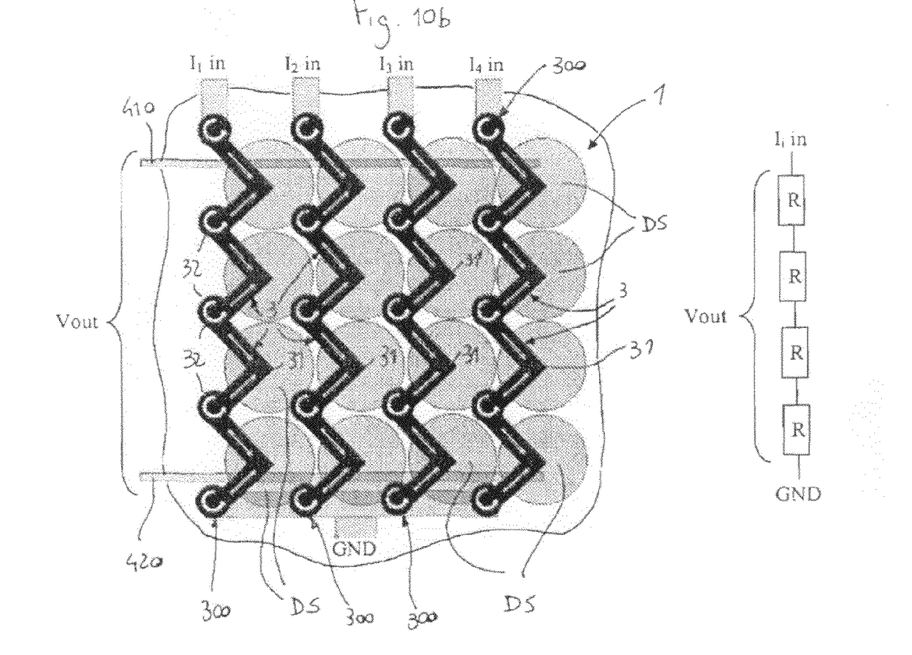

The dynamic range of the arrays, employing the units in FIGS. 10*a* and 10*b* can be easily assessed. The maximum concentration of detectable nanoparticles is in the order of $5 \cdot 10^8$ nanoparticles/$cm^2$, corresponding to a nanoparticle in each detection area 31. Instead, if 70 array units are used, arranged in an area of about 200 $\mu m^2$, functionalized with the same binding molecule, an array is obtained, which is able to detect only one molecule thereon, i.e. a concentration in the order of $5 \cdot 10^5$ nanoparticles/$cm^2$.

Obviously, provided the principle of the invention, the features of construction and the embodiments will be widely able to be varied in respect to what described and illustrated merely by way of example, without departing the scope of the invention.

The invention claimed is:

1. A magnetic nanoparticle presence detecting sensor, comprising:
    a support;
    a sensor body arranged on the support and including a planar ferromagnetic nanostructure having a detection area shaped as a strip bent to form a corner, the sensor body being structured to apply a magnetic field to cause the detection area to selectively assume, in response to the applied magnetic field:
        a first spin configuration comprising a transverse head-to-head domain wall (TW), and
        a second spin configuration, wherein a domain wall is absent, the transition from the first spin configuration to the second spin configuration being provided for the applied magnetic field, having a component which is parallel to one of an angled side of the detection area with an intensity greater than a predictable transition threshold, the transition threshold being magneto-resistively detectable and affected by a proximity of a magnetic nanoparticle to the detection area,
    a plurality of non-magnetic contacts arranged on the support and electrically conductively connected to the sensor body; and a measuring device which measures a magnetoresistance, the device arranged on the sensor and connected to the plurality of non-magnetic contacts, the measuring device being structured to provide a measure of the transition threshold by way of measures of the magneto-resistance of the detection area in the first spin configuration and the second spin configuration assumed upon application of the magnetic field.

2. The magnetic nanoparticle presence detecting sensor of claim 1, wherein the sensor body is structured so that the transition between the first spin configuration and the second spin configuration is due to an anisotropic magneto-resistance effect.

3. The magnetic nanoparticle presence detecting sensor of claim 1, further comprising a relative terminal disc arranged at opposite ends of the detection area.

4. The magnetic nanoparticle presence detecting sensor of claim 3, wherein the non-magnetic contacts comprise:
- a pair of injection contacts arranged from the opposite ends of the detection area and adapted to enable an injection of an electric current through the detection area; and
- a pair of reading contacts arranged from the opposite ends of the detection area and which are adapted to enable a measurement of a potential difference between the opposite ends of the detection area.

5. The magnetic nanoparticle presence detecting sensor of claim 1, wherein in the first spin configuration, the head-to-head domain wall traps and trails a magnetic nanoparticle towards the detection area.

6. The magnetic nanoparticle presence detecting sensor of claim 1, wherein the sensor body is arranged for one of: performing single molecule detection, synthesis at a single molecule level, and analysis at a single molecular level.

7. The magnetic nanoparticle presence detecting sensor of claim 1, wherein the sensor body is arranged for performing single molecule detection, synthesis at a single molecule level, and analysis at a single molecular level.

8. A sensor array for detecting target molecules to which magnetic nanoparticles are bound as markers, the sensor array comprising:
- a support provided with a plurality of detection sites to which respective binding molecules are associated, adapted to selectively bind with the target molecules, and respective sensors each being adapted to detect a presence of a magnetic nanoparticle in the respective detection site, each sensor including:
  - a sensor body arranged on the support and including a planar ferromagnetic nanostructure having a detection area shaped as a strip bent to form a corner, the sensor body being structured to apply a magnetic field to cause the detection area to selectively assume, in response to the applied magnetic field:
    - a first spin configuration comprising a transverse head-to-head domain wall (TW), and
    - a second spin configuration, wherein a domain wall is absent, the transition from the first spin configuration to the second spin configuration being provided for the applied magnetic field, having a component which is parallel to one of an angled side of the detection area with an intensity greater than a predictable transition threshold, the transition threshold being magneto-resistively detectable and affected by a proximity of a magnetic nanoparticle to the detection area;
  - a plurality of non-magnetic contacts arranged on the support and electrically conductively connected to the sensor body; and
  - a measuring device which measures a magnetoresistance, the device arranged on the sensor and connected to the plurality of non-magnetic contacts, the measuring device being structured to provide a measure of the transition threshold by way of measures of the magneto-resistance of the detection area in the first spin configuration and the second spin configuration assumed upon application of the magnetic field.

9. The sensor array of claim 8, wherein the sensors are arranged to form a plurality of sensor chains provided side-by-side.

10. The sensor array of claim 9, wherein each sensor chain comprises a plurality of the nanostructures.

11. The sensor array of claim 10, wherein the detection of each nanostructure is shaped as a strip bent to form a corner, at the ends of which respective terminal discs are placed.

12. The sensor array of claim 11, wherein the nanostructures are connected such that each nanostructure shares a common terminal disc with an adjacent nanostructure.

13. The sensor array of claim 12, wherein the non-magnetic contacts comprise:
- a plurality of injection contacts adapted to enable an injection of an electric current through the detection area of each nanostructure; and
- a plurality of reading contacts adapted to enable a measurement of a potential difference between the opposite ends of the detection area of each nanostructure.

14. The sensor array of claim 13, wherein the reading contacts are arranged such that the detection areas of the nanostructures, corresponding in position on different sensor chains, are connected in parallel.

15. The sensor array of claim 14, wherein the sensor chains are connected in parallel to a pair of the injection contacts to allow a simultaneous injection of respective electric currents through the sensor chains.

16. The sensor array of claim 13, wherein the reading contacts are arranged such that the detection areas of each sensor chain are connected in series.

17. The sensor array of claim 16, wherein each sensor chain is connected to a respective one of the injection contacts to allow an independent injection of a respective electric current through each sensor chain.

18. A method to detect target molecules to which magnetic nanoparticles as markers are linked, the method comprising:
- providing a sensor array,
- obtaining the first spin configuration in each nanostructure by applying a first magnetic field, and then removing the first magnetic field;
- delivering a biological sample containing the target molecules above the detection sites;
- switching the first spin configuration to the second spin configuration in each nanostructure by applying a second magnetic field, and then removing the second magnetic field;
- removing the target molecules not chemically linked to the binding molecules from the detection sites;
- obtaining the first spin configuration in each nanostructure by applying a third magnetic field, and then removing the third magnetic field; and then
- measuring the critical transition field from the first spin configuration into the second spin configuration through magneto-resistance measurements on the sensors, through said plurality of contacts.

* * * * *